US012698475B2

(12) United States Patent
O'Neil et al.

(10) Patent No.: US 12,698,475 B2
(45) Date of Patent: Aug. 4, 2026

(54) LYMPHOCYTES LACKING PERFORIN FUNCTION

(71) Applicant: VANDERBILT UNIVERSITY, Nashville, TN (US)

(72) Inventors: Richard T. O'Neil, Nashville, TN (US); Matthew H. Wilson, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 754 days.

(21) Appl. No.: 17/996,963

(22) PCT Filed: Apr. 26, 2021

(86) PCT No.: PCT/US2021/029142
§ 371 (c)(1),
(2) Date: Oct. 24, 2022

(87) PCT Pub. No.: WO2021/222092
PCT Pub. Date: Nov. 4, 2021

(65) Prior Publication Data
US 2023/0174934 A1 Jun. 8, 2023

Related U.S. Application Data

(60) Provisional application No. 63/015,932, filed on Apr. 27, 2020.

(51) Int. Cl.
*C12N 5/0783* (2010.01)
*A61K 40/11* (2025.01)
*A61K 40/42* (2025.01)
*C12N 15/90* (2006.01)

(52) U.S. Cl.
CPC ............ *C12N 5/0636* (2013.01); *A61K 40/11* (2025.01); *A61K 40/42* (2025.01); *C12N 15/907* (2013.01); *A61K 2239/31* (2023.05); *A61K 2239/55* (2023.05); *C12N 2510/00* (2013.01)

(58) Field of Classification Search
CPC .......................... C12N 5/0636; C12N 15/907; C12N 2510/00; A61K 40/11; A61K 40/42; A61K 2239/31; A61K 2239/55
See application file for complete search history.

(56) References Cited

U.S. PATENT DOCUMENTS

| | | |
|---|---|---|
| 6,713,055 B2 | 3/2004 | Schiff |
| 8,008,449 B2 | 8/2011 | Korman et al. |
| 8,552,154 B2 | 10/2013 | Freeman et al. |
| 8,617,546 B2 | 12/2013 | Kang et al. |
| 2015/0218150 A1 | 8/2015 | Spicer et al. |
| 2016/0176968 A1 | 6/2016 | Chang et al. |
| 2019/0192566 A1 | 6/2019 | Bertoletti et al. |
| 2019/0307798 A1 | 10/2019 | Kruse et al. |

FOREIGN PATENT DOCUMENTS

| | | |
|---|---|---|
| WO | 2015/039523 A1 | 3/2015 |
| WO | 2015/066262 A1 | 5/2015 |
| WO | 2019/147604 A2 | 8/2019 |

OTHER PUBLICATIONS

Wikipedia contributors. "Gene silencing." Wikipedia, The Free Encyclopedia. Wikipedia, The Free Encyclopedia, Jul. 16, 2025. Web. Aug. 2, 2025. (Year: 2025).*
Spicer, J.A., et al., 2017. Benzenesulphonamide inhibitors of the cytolytic protein perforin. Bioorganic & Medicinal Chemistry Letters, 27(4), pp. 1050-1054. (Year: 2017).*
Rosenberg, Steven A., et al., "Durable Complete Responses to Heavily Pretreated Patients with Metastatic Melanoma Using T-Cell Transfer Immunotherapy," Clinical Cancer Research, vol. 17, No. 13 (2011), pp. 4550-4557.
Dudley, Mark E., et al., "Cancer Regression and Autoimmunity in Patients After Clonal Repopulation with Antitumor Lymphocytes," Science, vol. 298 (2002), pp. 850-854.
Dudley, Mark E., et al., "Adoptive Cell Therapy for Patients With Metastatic Melanoma: Evaluation of Intensive Myeloablative Chemoradiation Preparative Regimens," Journal of Clinical Oncology, vol. 26, No. 32 (2008), pp. 5233-5239.
Dudley, Mark. E., et al., "Generation of Tumor-Infiltrating Lymphocyte Cultures for Use in Adoptive Transfer Therapy for Melanoma Patients," Journal of Immunotherapy, vol. 26, No. 4 (2003), pp. 332-342.
Godfrey, James, et al., "The role of natural killer cells in immunity against multiple myeloma," Leukemia & Lymphoma, vol. 53 (2012), pp. 1666-1676.
Narni-Mancinelli, Emilie, et al., "The 'T-cell-ness' of NK cells: unexpected similarities between NK cells and T cells," International Immunology, vol. 23, No. 7 (2011), pp. 427-431.
Morgan, Richard A., et al., "Case Report of a Serious Adverse Event Following the Administration of T Cells Transduced With a Chimeric Antigen Receptor Recognizing ERBB2," Molecular Therapy, vol. 18, No. 4 (2010), pp. 843-851.

(Continued)

*Primary Examiner* — Jeremy C Flinders
*Assistant Examiner* — Masudur Rahman
(74) *Attorney, Agent, or Firm* — Thomas Horstemeyer LLP.

(57) ABSTRACT

Disclosed herein are engineered cell-based peptide delivery platforms based on T cells lacking Perforin function. Perforin-null T cells lack cytotoxic effector function and thus are not capable of killing target cells by conventional Perforin dependent pathways. However, they efficiently home to target tissues where they can invade, persist, and proliferate. The homing ability of perforin lacking T cells can therefore be used to deliver anti-cancer or pre-immune peptides to tumors, or therapeutic peptides to other target tissues based on antigen recognition. Because the cells lack cytotoxic effector function due to loss, knockdown, or inhibition of Perforin, they can be targeted to tissues based on antigen recognition without destroying the target tissue directly.

14 Claims, 14 Drawing Sheets

(56) References Cited

OTHER PUBLICATIONS

Porter, David L., et al., "Chimeric Antigen Receptor-Modified T Cells in Chronic Lymphoid Leukemia," The New England Journal of Medicine, vol. 365, No. 8 (2011), pp. 725-733.

Godfrey, James, et al., "The role of natural killer cells immunity against multiple myeloma," Leukemia & Lymphoma, vol. 53, No. 9 (2012), pp. 1666-1676.

Fauriat, C., et al., Comments to the Editor for "Impaired activating receptor expression pattern in natural killer cells from patients with multiple myeloma," Leukemia, vol. 20 (2006), pp. 732-733.

Sadelain, Michel, et al., "Targeting Tumours with Genetically Enhanced T Lymphocytes," Nature Reviews, vol. 3 (2003), pp. 35-45.

Fresnak, Andrew D., et al., "Engineered T cells: the promise and challenges of cancer immunotherapy," Nature, vol. 16 (2016), pp. 566-581.

Imai, C., et al., "Chimeric receptors with 4-1BB signaling capacity provoke potent cytotoxicity against acute lymphoblastic leukemia," Leukemia, vol. 18 (2004), pp. 676-684.

Maher, John, et al., "Human T-lymphocyte cytotoxicity and proliferation directed by a single chimeric TCR/CD28 receptor," Nature Biotechnology, vol. 20 (2002), pp. 70-75.

Woof, Jenny M., et al., "Human Antibody-FC Receptor Interactions Illuminated By Crystal Structures," Nature Reviews, vol. 4 (2004), pp. 1-11.

Rosenberg, Steven A., et al., "Use of Tumor-Infiltrating Lymphycytes and Interleukin-2 in the Immunotherapy of Patients with Metastatic Melanoma," The New England Journal of Medicine, vol. 319, No. 25 (1988), pp. 1676-1680.

International Search Report and Written Opinion, PCT/US2021/029142, mailed Oct. 22, 2021 (17 pages).

* cited by examiner

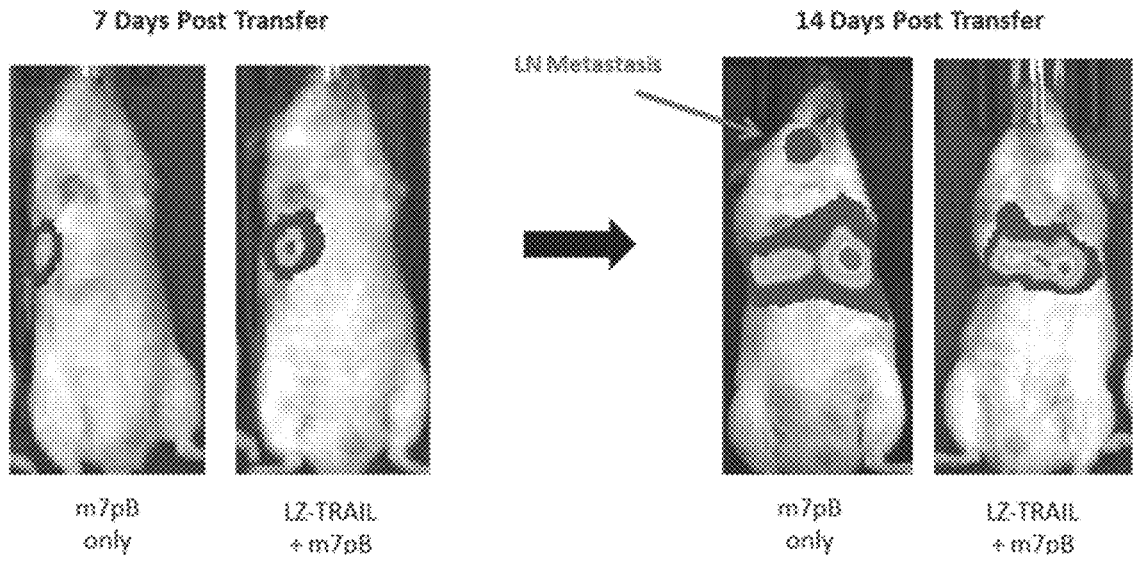
FIG. 3
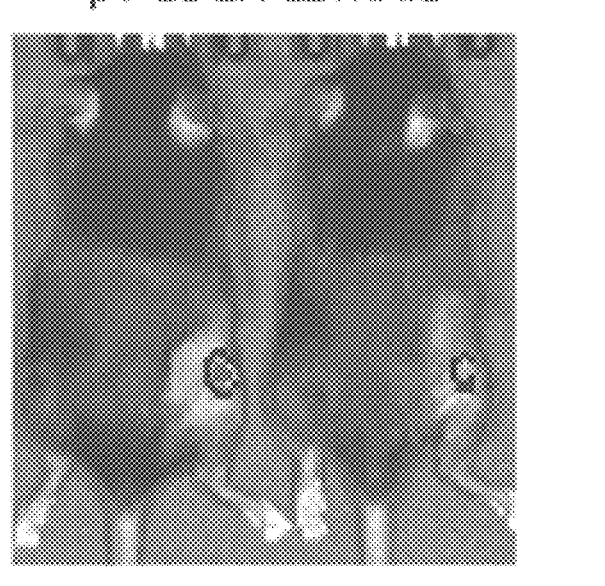
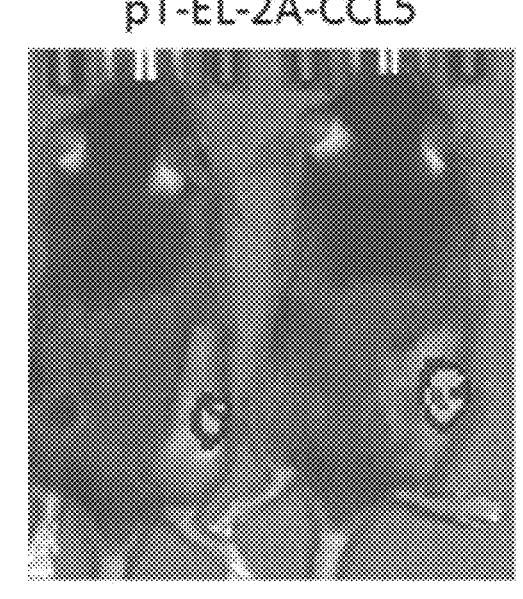
FIG. 4A                    FIG. 4B pT-EL-thy1.1: Luciferase transposon allowing for in vivo imaging if engineered cells

Prf+ OT1 T cells control          pT-EL-thy1.1

Day 11

Prf- OT1 T cells pT-EL-thy1.1

Enhanced Luciferase (EL)
expressing Prf- T cells migrate
to subcutaneous OVA+ tumors Prf- OT1 T cells pT-EL-2A-CCL5                    pT-EL-thy1.1

% of CD103+ DC (CD45+/CD11C+/MHCII+)

LYMPHOCYTES LACKING PERFORIN FUNCTION

CROSS-REFERENCE TO RELATED APPLICATIONS

This application claims benefit of U.S. Provisional Application No. 63/015,932, filed Apr. 27, 2020, which is hereby incorporated herein by reference in its entirety.

STATEMENT REGARDING FEDERALLY SPONSORED RESEARCH OR DEVELOPMENT

This invention was made with Government Support under Grant No. DK093660 awarded by the National Institutes of Health. The Government has certain rights in the invention.

BACKGROUND

The development of many tumor targeted CAR-T and TCR based cancer therapies have been limited because most tumor associated antigens are also expressed on normal healthy tissues. Thus, infused engineered cytotoxic T cells will also destroy normal tissue leading to potentially deadly "on-target/off-tumor" side effects.

SUMMARY

Disclosed herein are engineered cell-based peptide delivery platforms based on T cells lacking Perforin function. Perforin-null T cells lack cytotoxic effector function and thus are not capable of killing target cells by conventional Perforin dependent pathways. However, they efficiently home to target tissues where they can invade, persist, and proliferate. The homing ability of perforin lacking T cells can therefore be used to deliver anti-cancer or pre-immune peptides to tumors, or therapeutic peptides to other target tissues based on antigen recognition. Because the cells lack cytotoxic effector function due to loss, knockdown, or inhibition of Perforin, they can be targeted to tissues based on antigen recognition without destroying the target tissue directly.

In the context of cancer, the disclosed Perforin-null T cells can be used to deliver anti-cancer peptide payloads to solid tumors based on tumor associated antigens that could not be safely targeted using conventional cytotoxic T cells due to clinically intolerable side effects of 'on-target/off-tumor' cytotoxicity. This could expand the repertoire of potential tumor antigens that could be exploited for tumor targeted cell therapies. For example, type III of variant epidermal growth factor receptor (EGFRvIII), among others, can be targeted using the disclosed Perforin-null T cells with reduced off-tumor side effects.

In the context of autoimmune disease or acute injury induced tissue damage, T cells lacking perforin function could be used for more efficient targeted delivery of anti-inflammatory cytokines or other therapeutic peptides to effected tissues based on antigen expression.

In the context of systemic peptide delivery, Perforin-null T cells could be used to deliver therapeutic peptides by inducing engraftment of a stable memory population of these cells which have been engineered to produce a therapeutic peptide.

In the context of a persistent cell based vaccine, Perforin-null T cells could be engineered to express an antigen or other ligand that activates the T cell and induces proliferation thereby generating a self-sustaining pool of antigen expressing T cells that could be used as a persistent cellular vaccine.

Therefore, disclosed herein is a non-cytotoxic lymphocyte for adoptive cell therapy that has been engineered to have reduced or silenced perforin expression or activity. The disclosed lymphocyte can therefore be used to deliver a cargo molecule to a target cell without the risk of off-target cytotoxic function. In some embodiments, the disclosed lymphocyte has also been engineered to express at least one therapeutic nucleic acid or polypeptide for delivery to target cells. Also disclosed herein is a method for reducing cytotoxicity of a lymphocyte that involves administering to the lymphocyte an effective amount of a perforin inhibitor. Also disclosed herein is a method for treating a disease or disorder, such as cancer, in a subject that involves administering to the subject an effective amount of the recombinant lymphocyte disclosed herein Perforin expression can be silenced or reduced using a variety of known techniques, such as genetic ablation of the perforin gene using protein or ribonucleoprotein targeting (TALEN, Zinc-finger, ACRUS, Cas9 or other programable nuclease) with or without HDR repair templates allowing for further screening, enrichment by selective expansion or protection using a negative selectable marker, recombinant expression of miRNA or shRNA targeting the perforin gene RNA for knockdown, or stable recombinant expression of a dominant negative perforin molecule that blocks assembly of functional pores.

Therefore, in some embodiments, perforin expression has been silenced with an siRNA, shRNA, gRNA, or antisense oligonucleotide with complementary binding to PRF1 genomic DNA or mRNA. In some embodiments, perforin expression has been knocked out by homologous recombination or gene editing of the PRF1 gene. In some embodiments, perforin activity has been inhibited with a benzene-sulphonamide-based perforin inhibitor.

The disclosed compositions and methods can be used to reduce cytotoxicity of any lymphocyte. For example, in some embodiments, the lymphocyte is a T cell, Tumor Infiltrating Lymphocyte (TIL), an Antibody-Coupled T cell Receptor (ACTR), or a natural killer (NK) cell. The lymphocyte can be autologous or allogeneic so long as it is rendered safe for transplantation. In some embodiments, the lymphocyte is an off-the shelf recombinant lymphocyte that has been engineered by the disclosed methods to be non-cytotoxic.

In some embodiments, the disclosed recombinant lymphocyte is further engineered to express a targeting molecule for delivery of the cargo molecule to a target cell. For example, in some embodiments, the targeting molecule is a ligand, receptor, antibody, or fragment thereof capable of binding a target cell. In some embodiments, the targeting molecule is a bi-specific antibody. In some embodiments, the targeting molecule is a chimeric antigen receptor (CAR) or a modified T cell receptor (TCR).

In some embodiments, the cargo molecule is a therapeutic nucleic acid or polypeptide/peptide/protein. For example, in some embodiments, the therapeutic polypeptide is an anti-cancer peptide. In some embodiments, the therapeutic polypeptide is a cytokine or chemokine, such as IL2, IL12, IL21, TRAIL, CCL5, GM-CSF, Flt3L, IFN$\alpha$, or IFN$\gamma$. In some embodiments, the therapeutic polypeptide is selected from the group consisting of erythropoietin, EGF, alpha-galactosidase A (and other enzyme deficiencies), insulin, fibroblast growth factor 21 [FGF21], $\alpha$Klotho, and soluble transforming growth factor-$\beta$ receptor 2 (sTGF$\beta$R2). In some embodiments, the therapeutic nucleic acid or polypeptide is an antigen or ligand, wherein the non-cytotoxic lymphocyte functions as a cellular vaccine.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic representation of adoptive transfer approaches. FIG. 1B shows in vivo luciferase imaging showing efficient engraftment of engineered T cells. Plasmid vaccine: Adoptive transfer of $10^7$ pT-EL-Thy1.1 modified OT1 T cells followed by subdermal plasmid vaccination with pT-CAGOVA and pCMV-M7pB. T cell vaccine: Adoptive transfer of $10^7$ pT-EL-Thy1.1 modified OT1 T cells concomitantly with $10^6$ pTCAG-OVA modified OT1 T cells.

FIG. 2A is a schematic representation of experimental strategy for delivering erythropoietin (EPO) using engineered antigen-specific T cells. FIG. 2B shows stable engraftment of T cells engineered to produce EPO results in elevation of hematocrit (HCT) for more than 4 months after adoptive transfer. FIG. 2C shows serum EPO levels as measured by ELISA after adoptive transfer of EPO engineered T cells. Red arrows indicate administration of cellular vaccine 'booster'.

FIG. 3 contains representative images showing xenografts and lymphatic metastasis. Mice received injections of 2.5× $10^5$ Luciferase expressing LLC cells into the lung. On the same day, these mice also received adoptive transfers of 1×$10^7$ OT1 T cells that were transfected with pCMV-m7pB (piggyBac transposase) only, or 1×$10^7$ OT1 T cells transfected with pT-CMV-(LZ)TRAIL transposon and pCMVm7pB transposase. In vivo luciferase imaging allows direct observation of metastasis.

FIGS. 4A to 4C show Prf$^{Null}$ OT1 cells expressing pT-EL-LZTRAIL or pT-EL-CCL5 home to OVA+tumors. Mice were adoptively transferred with transposon modified OT1 Prf$^{Null}$ T cells expressing TRAIL (FIG. 4A) or CCL5 (FIG. 4B) 24 hours prior to subcutaneous engraftment of LLC-OVA tumors. Luciferase signal indicates that modified Prf$^{Null}$ OT1 cells home to OVA+ tumors. FIG. 4C show T cells transfected with pT-EL-CCL5 or pT-EL-thy1.1 and CCL5 was measured in media by ELISA.

FIG. 6A shows schematic representation of the transposon used to engineer T cells in this study. (CMV: cytomegalovirus promoter; Luciferase: enhanced firefly luciferase; IRES:

internal ribosomal entry site; WPRE: woodchuck poxvirus response element; SV40pA: polyadenylation sequence derived from SV40. FIG. 6B shows luciferase imaging from mice 48 h after adoptive transfer of 5 million luciferase modified OT1 T cells transferred to mice bearing OVA expressing B16 melanoma tumors. FIG. 6C shows luciferase imaging from mice 48 hours after adoptive transfer of 5 million luciferase modified Perforin-KO OT1 T cells.

FIGS. 7A to 7C show tumor targeted Prf-T cells engineered to express CCL5 enhance cDC1 infiltration. FIG. 7A shows in vivo imaging demonstrating that Prf-OT1 T cells efficiently home to tumors even when engineered to over express CCL5. FIG. 7B shows flow cytometry was conducted to test the hypothesis that cDC1 dendritic cells are recruited into MC38 tumors and that this is augmented by delivery of CCL5 using Prf-OT1 T cells. FIG. 7C is a schematic of proposed mechanism for facilitating dendritic cell recruitment into solid tumors mediated by Prf-OT1 transposon engineered to express CCL5.

FIG. 8A is a schematic diagram of experimental approach and timeline. Mice were subjected to lymphodepleting irradiation and on the following day they were adoptively transferred with 8 million Prf-OT1 that were transposon engineered to express luciferase. The mice were imaged following adoptive transfer to confirm engraftment. Contraction of T cells was confirmed by imaging at day 35 post adoptive transfer. A hydrodynamic vaccine injection (Hdx) of plasmids driving expression of either GFP (negative control) or chicken ovalbumin peptide which. FIG. 8B, left panels show mice luciferase imaging of mice 5 days after adoptive transfer. FIG. 8B, center panels are images of the same mice on day 35 after transfer. FIG. 8B, left panels are mice imaged 24 hours after adoptive transfer. Note extensive liver infiltration of T cells in OVA group and absence of T cells in GFP group indicating that the response is OVA specific. FIG. 8C shows in vivo plot 3D reconstruction of luciferase signal 5 days after OVA vaccine confirming liver localization of Prf-T cells.

DETAILED DESCRIPTION

Figure 1A:
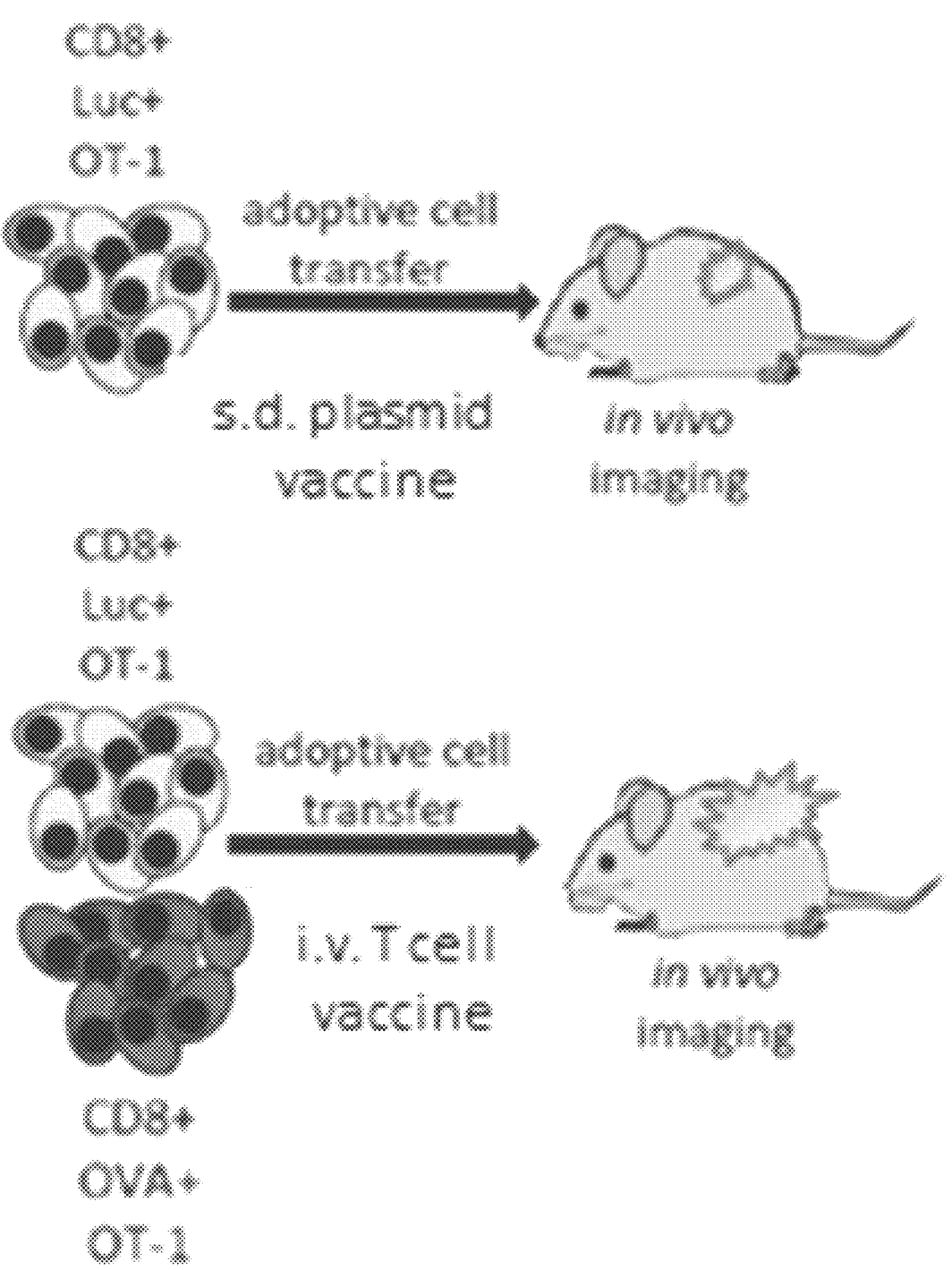
FIGS. 1A and 1B show adoptive transfer of antigen-specific T cells augmented by cellular vaccine results in efficient long term engraftment.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "agent" or "compound" as used herein refers to a chemical entity or biological product, or combination of chemical entities or biological products, administered to a subject to treat or prevent or control a disease or condition. The chemical entity or biological product is preferably, but not necessarily a low molecular weight compound, but may also be a larger compound, or any organic or inorganic molecule, including modified and unmodified nucleic acids such as antisense nucleic acids, RNAi, such as siRNA or shRNA, peptides, peptidomimetics, receptors, ligands, and antibodies, aptamers, polypeptides, nucleic acid analogues or variants thereof. For example, an agent can be an oligomer of nucleic acids, amino acids, or carbohydrates including, but not limited to proteins, peptides, oligonucleotides, ribozymes, DNAzymes, glycoproteins, RNAi agents (e.g., siRNAs), lipoproteins, aptamers, and modifications and combinations thereof. In some embodiments, an active agent is a nucleic acid, e.g., miRNA or a derivative or variant thereof.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The terms "peptide," "protein," and "polypeptide" are used interchangeably to refer to a natural or synthetic molecule comprising two or more amino acids linked by the carboxyl group of one amino acid to the alpha amino group of another.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

A "ligand", as used herein, refers generally to all molecules capable of reacting with or otherwise recognizing or binding to a receptor on a target cell.

Perforin-Null Lymphocytes

Disclosed herein are lymphocytes that have been engineered to have reduced or silenced perforin expression or activity. The lymphocytes can be further engineered, e.g. to express at least one therapeutic nucleic acid or polypeptide, at least one targeting molecule, and the like.

Accordingly, in some embodiments, an isolated lymphocyte is provided. The disclosed lymphocytes are engineered to have reduced perforin expression and/or activity (referred to herein as "Perforin-null lymphocytes"). In certain embodiments, the isolated lymphocyte is a T cell, an NK cell, a B cell, a tumor infiltrating lymphocyte (TIL), a chimeric antigen receptor T cell (CAR-T cell), a TCR-engineered T cell (TCR-T cell), a TCR CAR-T cell, a CAR TIL cell, a CAR-NK cell, or a hematopoietic stem cell that gives rise to a lymphocyte cell. In other embodiments, the cell is a stem cell, a dendritic cell, and the like.

In some embodiments, the Perforin-null lymphocytes are targeted to cancerous cells from various types of cancers. Such cancers include, without limitation, prostate cancers; ovarian cancers; cervical cancers; colorectal cancers; intestinal cancers; testicular cancers; skin cancers; lung cancers; thyroid cancers; bone cancers; breast cancers; bladder cancers; uterine cancers; vaginal cancers; pancreatic cancers; liver cancers; kidney cancers; brain cancers; spinal cord cancers; oral cancers; parotid tumors; blood cancers; lymphomas, solid tumors, liquid tumors, etc. In some embodiments, other cell proliferative disorders are treated, including precancerous conditions; hematologic disorders; and immune disorders, such as autoimmune disorders including, without limitation, Addison's disease, celiac disease, diabetes mellitus type 1, Grave's disease, Hashimoto's disease, inflammatory bowel disease, multiple sclerosis, psoriasis, rheumatoid arthritis, scleroderma, and systemic lupus erythematosus.

Lymphocytes for use in the disclosed compositions and methods are preferably obtained from the subject to be treated (i.e. are autologous). However, in some embodiments, stem cells, lymphocyte cell lines or donor cells (allogeneic) are used. Lymphocytes can be obtained from a number of sources, including peripheral blood mononuclear cells, bone marrow, lymph node tissue, cord blood, thymus tissue, tissue from a site of infection, ascites, pleural effusion, spleen tissue, and tumors. Lymphocytes can be obtained from blood collected from a subject using any number of techniques known to the skilled artisan, such as Ficoll™ separation. For example, cells from the circulating blood of an individual may be obtained by apheresis. In some embodiments, lymphocytes are isolated from peripheral blood lymphocytes by lysing the red blood cells and depleting the monocytes, for example, by centrifugation through a PERCOLL™ gradient or by counterflow centrifugal elutriation. A specific subpopulation of lymphocytes can be further isolated by positive or negative selection techniques. For example, lymphocytes can be isolated using a combination of antibodies directed to surface markers unique to the positively selected cells, e.g., by incubation with antibody-conjugated beads for a time period sufficient for positive selection of the desired immune effector cells. Alternatively, enrichment of lymphocyte population can be accomplished by negative selection using a combination of antibodies directed to surface markers unique to the negatively selected cells.

Lymphocyte activation occurs when lymphocytes are triggered through antigen-specific receptors on their cell surface. This causes the cells to proliferate and differentiate into specialized effector lymphocytes. Such "activated" lymphocytes are typically characterized by a set of receptors on the surface of the lymphocyte. Surface markers for activated T cells include CD3, CD4, CD8, PD1, IL2R, and others. Activated cytotoxic lymphocytes can kill target cells after binding cognate receptors on the surface of target cells.

Lymphocytes for use in the disclosed compositions and methods include T cells for cell-mediated, cytotoxic adaptive immunity, such as CD4+ and/or CD8+ cytotoxic T cells; NK cells that function in cell-mediated, cytotoxic innate immunity; and B cells for humoral, antibody-driven adaptive immunity. Also included are hematopoietic stem cells that gives rise to lymphoid cells. Additionally, CAR-T cells, TCR cells, including TCR engineered CAR-T cells, TILs, CAR TILs, CAR-NK cells, and the like, can be modified using the techniques herein.

Lymphocytes for modification can be isolated from a subject, such as a human subject, for example from blood or from solid tumors, such as in the case of TILs, or from lymphoid organs such as the thymus, bone marrow, lymph nodes, and mucosal-associated lymphoid tissues. Techniques for isolating lymphocytes are well known in the art. For example, lymphocytes can be isolated from peripheral blood mononuclear cells (PBMCs), which are separated from whole blood using, for example, Ficoll, a hydrophilic polysaccharide that separates layers of blood, and density gradient centrifugation. Generally, anticoagulant or defibrinated blood specimens are layered on top of a Ficoll solution, and centrifuged to form different layers of cells. The bottom layer includes red blood cells (erythrocytes), which are collected or aggregated by the Ficoll medium and sink completely through to the bottom. The next layer contains primarily granulocytes, which also migrate down through the Ficoll-paque solution. The next layer includes lymphocytes, which are typically at the interface between the plasma and the Ficoll solution, along with monocytes and platelets. To isolate the lymphocytes, this layer is recovered, washed with a salt solution to remove platelets, Ficoll and plasma, then centrifuged again.

Other techniques for isolating lymphocytes include biopanning, which isolates cell populations from solution by binding cells of interest to antibody-coated plastic surfaces. Unwanted cells are then removed by treatment with specific antibody and complement. Additionally, fluorescence activated cell sorter (FACS) analysis can be used to detect and count lymphocytes. FACS analysis uses a flow cytometer that separates labelled cells based on differences in light scattering and fluorescence.

For TILs, lymphocytes are isolated from a tumor and grown, for example, in IL-2 and selected using cytokine release coculture assays against either autologous tumor or HLA-matched tumor cell lines. Cultures with evidence of increased specific reactivity compared to allogeneic non-MHC matched controls are selected for rapid expansion and then introduced into a subject in order to treat cancer. See, e.g., Rosenberg et al., Clin. Cancer Res. (2011) 17:4550-4557; Dudly et al., Science (2002) 298:850-854; Dudly et al., J. Clin. Oncol. (2008) 26:5233-5239; Dudley et al., J. Immnother. (2003) 26:332-342.

Upon isolation, lymphocytes can be characterized in terms of specificity, frequency and function. Frequently used assays include an ELISPOT assay, which measures the frequency of T cell response.

In some embodiments, lymphocytes for modification are isolated from a subject, modified in vitro, and then reintroduced into the same subject. This technique is known as autologous lymphocyte therapy. Alternatively, lymphocytes can be isolated, modified in vitro, and introduced into a different subject. This technique is known as allogenic lymphocyte therapy.

After isolation, lymphocytes can be activated using techniques well known in the art in order to promote proliferation and differentiation into specialized effector lymphocytes. Surface markers for activated T cells include, for example, CD3, CD4, CD8, PD1, IL2R, and others. Activated cytotoxic lymphocytes can kill target cells after binding cognate receptors on the surface of target cells. Surface markers for K cells include, for example CD16, CD56, and others.

Following isolation and optionally activation, lymphocytes are modified in order to express one or more endogenous chemokine receptor genes present in the lymphocyte genome that are normally epigenetically silenced. When expressed, the chemokine receptor presents on the lymphocyte cell surface and is specific for, and targets, the lymphocyte to a cognate chemokine present on the tumor cell surface or secreted by the tumor microenvironment.

Lymphocytes can be screened to select for cells expressing the desired cell surface receptor, using methods such as high-throughput screening techniques including, but not limited to, fluorescence-activated cell sorting (FACS)-based screening platforms, microfluidics-based screening platforms, and the like.

In some embodiments, the immune effector cells comprise any leukocyte involved in defending the body against infectious disease and foreign materials. For example, the immune effector cells can comprise lymphocytes, monocytes, macrophages, dendritic cells, mast cells, neutrophils, basophils, eosinophils, or any combinations thereof.

In some embodiments, the cells used are natural killer T (NKT) cells (not to be confused with natural killer (NK) cells), which bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the lymphocytes comprise a mixture of CD4+ and CD8+ cells. In other embodiments, the T cells are enriched for one or more subsets based on cell surface expression. For example, in some cases, the T comprise are cytotoxic CD8⁺ T lymphocytes. In some embodiments, the T cells comprise γδ T cells, which possess a distinct TCR having one γ chain and one δ chain instead of α and β chains.

In some embodiments, the cells used are primary or stem cell-derived NK cells. NK cells are CD56⁺CD3⁻ large granular lymphocytes that can kill virally infected and transformed cells, and constitute a critical cellular subset of the innate immune system (Godfrey J, et al. Leuk Lymphoma 2012 53:1666-1676). Unlike cytotoxic CD8⁺ T lymphocytes, NK cells launch cytotoxicity against tumor cells without the requirement for prior sensitization, and can also eradicate MHC-I-negative cells (Narni-Mancinelli E, et al. Int Immunol 2011 23:427-431). NK cells are safer effector cells, as they may avoid the potentially lethal complications of cytokine storms (Morgan R A, et al. Mol Ther 2010 18:843-851), tumor lysis syndrome (Porter D L, et al. N Engl J Med 2011 365:725-733), and on-target, off-tumor effects. Although NK cells have a well-known role as killers of cancer cells, and NK cell impairment has been extensively documented as crucial for progression of MM (Godfrey J, et al. Leuk Lymphoma 2012 53:1666-1676; Fauriat C, et al. Leukemia 2006 20:732-733), the means by which one might enhance NK cell-mediated anti-MM activity has been largely unexplored prior to the disclosed CARs.

Chimeric Antigen Receptors (CAR)

In some cases, the disclosed Perforin-null lymphocytes also express a chimeric receptor. In some embodiments, the chimeric receptor comprises a chimeric antigen receptor (CAR) polypeptide. CARs generally incorporate an antigen recognition domain from the single-chain variable fragments (scFv) of a monoclonal antibody (mAb) with transmembrane signaling motifs involved in lymphocyte activation (Sadelain M, et al. Nat Rev Cancer 2003 3:35-45). The disclosed CAR is generally made up of three domains: an ectodomain, a transmembrane domain, and an endodomain. The ectodomain comprises the recognition domain. It also optionally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain transmits an activation signal to the immune effector cell after antigen recognition. For example, the endodomain can contain an intracellular signaling domain (ISD) and optionally a co-stimulatory signaling region (CSR).

A "signaling domain (SD)" generally contains immunoreceptor tyrosine-based activation motifs (ITAMs) that activate a signaling cascade when the ITAM is phosphorylated. The term "co-stimulatory signaling region (CSR)" refers to intracellular signaling domains from costimulatory protein receptors, such as CD28, 41BB, and ICOS, that are able to enhance T-cell activation by T-cell receptors.

In some embodiments, the endodomain contains an SD or a CSR, but not both. In these embodiments, an immune effector cell containing the disclosed CAR is only activated if another CAR (or a TCR ectodomain) containing the missing domain also binds its respective antigen.

Additional CAR constructs are described, for example, in Fresnak A D, et al. Engineered T cells: the promise and challenges of cancer immunotherapy. Nat Rev Cancer. 2016 Aug. 23; 16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

TRUCKs (T cells redirected for universal cytokine killing) co-express a CAR and an antitumor cytokine. Cytokine expression may be constitutive or induced by T cell activation. Targeted by CAR specificity, localized production of pro-inflammatory cytokines recruits endogenous immune cells to tumor sites and may potentiate an antitumor response.

Universal, allogeneic CAR T cells are engineered to no longer express endogenous TCR and/or major histocompatibility complex (MHC) molecules, thereby preventing graft-versus-host disease (GVHD) or rejection, respectively.

Self-driving CARs co-express a CAR and a chemokine receptor, which binds to a tumor ligand, thereby enhancing tumor homing.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

Marked CAR T cells express a CAR plus a tumor epitope to which an existing monoclonal antibody agent binds. In the setting of intolerable adverse effects, administration of the monoclonal antibody clears the CAR T cells and alleviates symptoms with no additional off-tumor effects.

A tandem CAR (TanCAR) T cell expresses a single CAR consisting of two linked single-chain variable fragments (scFvs) that have different affinities fused to intracellular co-stimulatory domain(s) and a CD3ζ domain. TanCAR T cell activation is achieved only when target cells co-express both targets.

A dual CAR T cell expresses two separate CARs with different ligand binding targets; one CAR includes only the CD3ζ domain and the other CAR includes only the co-stimulatory domain(s). Dual CAR T cell activation requires co-expression of both targets on the tumor.

A safety CAR (sCAR) consists of an extracellular scFv fused to an intracellular inhibitory domain. sCAR T cells co-expressing a standard CAR become activated only when encountering target cells that possess the standard CAR target but lack the sCAR target.

The antigen recognition domain of the disclosed CAR is usually an scFv. There are however many alternatives. An antigen recognition domain from native TCR alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from CD8, CD3ζ, CD3δ, CD3γ, CD3ε, CD32 (Fc gamma RIIa), DAP10, DAP12, CD79a, CD79b, FcγRIγ, FcγRIIIγ, FcεRIβ (FCERIB), and FcεRIγ (FCERIG).

In particular embodiments, the intracellular signaling domain is derived from CD3 zeta (CD3ζ) (TCR zeta, GenBank accno. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3ζ chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. Preclinical studies have indicated that the second generation of CAR designs improves the antitumor activity of T cells. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3ζ signaling domain by itself or combined with any other desired cytoplasmic domain(s). For example, the cytoplasmic domain of the CAR can comprise a CD3ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD83, CD8, CD4, b2c, CD80, CD86, DAP10, DAP12, MyD88, BTNL3, and NKG2D. Thus, while the CAR is exemplified primarily with CD28 as the co-stimulatory signaling element, other costimulatory elements can be used alone or in combination with other co-stimulatory signaling elements.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety (e.g., anti-CD123 scFv) and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. Alternatively, the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

In some embodiments, the recognition domain is a single chain variable fragment (scFv) antibody. The affinity/specificity of an scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3).

In some embodiments, the recognition domain is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Also disclosed are bi-specific CARs that target two different antigens. Also disclosed are CARs designed to work only in conjunction with another CAR that binds a different antigen, such as a tumor antigen. For example, in these embodiments, the endodomain of the disclosed CAR can contain only a signaling domain (SD) or a co-stimulatory signaling region (CSR), but not both. The second CAR (or endogenous T-cell) provides the missing signal if it is activated. For example, if the disclosed CAR contains an SD but not a CSR, then the immune effector cell containing this CAR is only activated if another CAR (or T-cell) containing a CSR binds its respective antigen. Likewise, if the disclosed CAR contains a CSR but not a SD, then the immune effector cell containing this CAR is only activated if another CAR (or T-cell) containing an SD binds its respective antigen.

Tumor antigens are proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated. Tumor antigens are well known in the art and include, for example, a glioma-associated antigen, carcinoembryonic antigen (CEA), EGFRvIII, IL-IIRa, IL-13Ra, EGFR, FAP, B7H3, Kit, CA LX, CS-1, MUC1, BCMA, bcr-abl, HER2, β-human chorionic gonadotropin, alphafetoprotein (AFP), ALK, CD19, TIM3, cyclin BI, lectin-reactive AFP, Fos-related antigen 1, ADRB3, thyroglobulin, EphA2, RAGE-1, RUI, RU2, SSX2, AKAP-4, LCK, OY-TESI, PAX5, SART3, CLL-1, fucosyl GM1, GloboH, MN-CA IX, EPCAM, EVT6-AML, TGS5, human telomerase reverse transcriptase, plysialic acid, PLAC1, RUI, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LAGE-Ia, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFR-beta, survivin and telomerase, legumain, HPV E6, E7, sperm protein 17, SSEA-4, tyrosinase, TARP, WT1, prostate-carcinoma tumor antigen-1 (PCTA-1), ML-IAP, MAGE, MAGE-A1, MAD-CT-1, MAD-CT-2, MelanA/MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, TIM3, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRCSD, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, CD123, CD19, TIM3, BCMA, GD2, CLL-1, CA-IX, MUCI, HER2, and any combination thereof.

Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, pI85erbB2, pI80erbB-3, c-met, nm-23H1, PSA, CA 19-9, CA 72-4, CAM 17.1, NuMa, K-ras, beta-Catenin, CDK4, Mum-1, p 15, p 16, 43-9F, 5T4, 791Tgp72, alphafetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCASI, SDCCAG1 6, TA-90\Mac-2 binding protein\cyclophilm C-associated protein, TAAL6, TAG72, TLP, TPS, GPC3, MUC16, LMP1, EBMA-1, BARF-1, CS1, CD319, HER1, B7H6, L1CAM, IL6, and MET.

Exemplary CAR-T cells that can be modified as disclosed herein include those targeting CD19, CD20, CD22, CD30, CD33, CD138, CD171, CEA, CD123, IL13RA, EGFR, EGFRvIII, ErbB, FAP, GD2, Glypican 3, Her2, Mesothelin, ULBP and MICA/AB, PD1, MUC1, VEGF2, and ROR1.

Therapeutic Methods

The disclosed Perforin-null lymphocytes can be used for a number of therapeutic purposes, such as to elicit an anti-tumor immune response against cancer cells, function as a cellular vaccine, and/or deliver therapeutic cargo to a target cell. An anti-tumor immune response may be an active or a passive immune response. In addition, the immune response may be part of an adoptive immunotherapy approach in which modified lymphocytes induce an immune response specific to the target antigen.

Adoptive transfer of modified lymphocytes is a promising anti-cancer therapeutic. Following the collection of a patient's immune effector cells, the cells may be genetically engineered to express the disclosed inhibitors of T cell suppression, and optionally other proteins such as chimeric receptors, according to the disclosed methods, then infused back into the patient.

The disclosed chimeric effector cells may be administered either alone, or as a pharmaceutical composition in combination with diluents and/or with other components such as IL-2, IL-15, or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodiments formulated for intravenous administration. Pharmaceutical compositions may be administered in any manner appropriate to treat tumors. The quantity and frequency of administration will be determined by such factors as the condition of the patient, and the severity of the patient's disease, although appropriate dosages may be determined by clinical trials.

When "an immunologically effective amount", "an anti-tumor effective amount", "a tumor-inhibiting effective amount", or "therapeutic amount" is indicated, the precise amount of the compositions to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed Perforin-null lymphocytes are administered to a patient in conjunction with (e.g., before, simultaneously or following) any number of relevant treatment modalities, including but not limited to thalidomide, dexamethasone, bortezomib, and lenalidomide. In further embodiments, the modified lymphocytes may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM PATH. In another embodiment, the cell compositions are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells. In an additional embodiment, expanded cells are administered before or following surgery.

The cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed chimeric cells can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed Perforin-null lymphocytes can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed Perforin-null lymphocytes can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires TCR activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent is a targeted agent, such as ibrutinib or idelalisib.

In some embodiments, such an additional therapeutic agent is an epigenetic modifier such as azacitidine or vidaza.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbB1 (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec STI571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with Perforin-null lymphocytes for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-Ia from the human CXC and C-C chemokine families. Suitable cytokines include cytokine derivatives, cytokine variants, cytokine fragments, and cytokine fusion proteins.

In some embodiments, a therapeutic agent for use in combination with Perforin-null lymphocytes for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with Perforin-null lymphocytes for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with Perforin-null lymphocytes for treating the disorders as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed Perforin-null lymphocytes are administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed Perforin-null lymphocytes are administered in combination with surgery.

Pharmaceutical Compositions

Once produced, the Perforin-null lymphocytes can be formulated into compositions for delivery to the subject to be treated. Therefore, disclosed herein is a Perforin-null lymphocytes in a pharmaceutically acceptable excipient. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A pharmaceutical composition can also include an antimicrobial agent for preventing or deterring microbial growth. Nonlimiting examples of antimicrobial agents include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can also be present in the pharmaceutical composition. Antioxidants are used to prevent oxidation, thereby preventing the deterioration of the lymphocytes or other components of the preparation. Suitable antioxidants include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as TWEEN 20 and TWEEN 80, and pluronics such as F68 and F88 (BASF, Mount Olive, New Jersey); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The quantity of lymphocytes in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy," Current edition, Williams & Williams, the "Physician's Desk Reference," Current edition, Medical Economics, Montvale, NJ, and Kibbe, A. H., Handbook of Pharmaceutical Excipients, Current edition, American Pharmaceutical Association, Washington, D.C.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions will find use herein.

The pharmaceutical preparations can also be housed in a syringe, an implantation device, or the like, depending upon the intended mode of delivery and use. Preferably, the amount of the composition present is appropriate for a single dose, in a premeasured or prepackaged form.

The compositions herein may optionally include one or more additional agents, such as other medications used to treat a subject for the cancer in question or to treat known side-effects from the treatment. For example, T cells release cytokines into the bloodstream, which can lead to dangerously high fevers and precipitous drops in blood pressure. This condition is known as cytokine release syndrome (CRS). In many patients, CRS can be managed with standard supportive therapies, including steroids and immuno-therapies, such as tocilizumab (Actemra™, Genetech, South San Francisco, CA) that block IL-6 activity.

At least one therapeutically effective cycle of treatment with a modified lymphocyte composition will be administered to a subject. By "therapeutically effective cycle of treatment" is intended a cycle of treatment that, when administered, brings about a positive therapeutic response with respect to treatment of an individual for the disease in question. By "positive therapeutic response" is intended that the individual undergoing treatment exhibits an improvement in one or more symptoms of the disease, including such improvements as tumor reduction and/or reduced need for lymphocyte therapy.

In certain embodiments, multiple therapeutically effective doses of compositions comprising the lymphocytes or other medications will be administered. The disclosed compositions of the are typically, although not necessarily, administered via injection, such as subcutaneously, intradermally, intravenously, intraarterially, intramuscularly, intraperitoneally, intramedullary, intratumorally, intranodally), by infusion, or locally. The pharmaceutical preparation can be in the form of a liquid solution or suspension immediately prior to administration. The foregoing is meant to be exemplary as additional modes of administration are also contemplated. The pharmaceutical compositions may be administered using the same or different routes of administration in accordance with any medically acceptable method known in the art.

The actual dose to be administered will vary depending upon the age, weight, and general condition of the subject as well as the severity of the condition being treated, the judgment of the health care professional, and particular lymphocytes being administered. Therapeutically effective amounts can be determined by those skilled in the art, and will be adjusted to the particular requirements of each particular case.

Generally, a therapeutically effective quantity of lymphocytes will range from a total of about $1\times10^6$ to about $1\times10^{10}$ lymphocytes or more per patient, such as $1\times10^6$ to about $1\times10^{10}$, e.g., $1\times10^1$ to $1\times10^9$, or any amount within these ranges. The total number of lymphocytes can be administered in a single bolus dose, or can be administered in two or more doses, such as one or more days apart. The amount of compound administered will depend on the potency of the specific lymphocyte composition, the disease being treated and the route of administration. Additionally, the doses can comprise a mixture of lymphocytes, such as a mix of CD8+ and CD4+ cells. If a mix of CD8+ and CD4+ cells is provided, the ratio of CD8+ to CD4+ cells can be for example, 1:1, 1:2 or 2:1, 1:3 or 3:1, 1:4 or 4:1, 1:5 or 5:1, etc.

The Perforin-null lymphocytes can be administered prior to, concurrent with, or subsequent to other agents. If provided at the same time as other agents, the modified lymphocytes can be provided in the same or in a different composition. Thus, the lymphocytes and other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising modified lymphocytes and a dose of a pharmaceutical composition comprising at least one other agent, such as another chemotherapeutic agent, which in combination comprises a therapeutically effective dose, according to a particular dosing regimen. Similarly, modified lymphocytes and therapeutic agents can be administered in at least one therapeutic dose. Administration of the separate pharmaceutical compositions can be performed simultaneously or at different times (e.g., sequentially, in either order, on the same day, or on different days), as long as the therapeutic effect of the combination of these substances is caused in the subject undergoing therapy.

Kits

Also disclosed herein are kits for use in the disclosed methods. In certain embodiments, the kits comprise one or more containers comprising isolated Perforin-null lymphocytes, modified as described herein, or compositions comprising the lymphocytes. The containers may be unit doses, bulk packages (e.g., multi-dose packages), or subunit doses.

The kits may comprise the components in any convenient, appropriate packaging. For example, ampules with non-resilient, removable closures (e.g, sealed glass) or resilient stoppers are most conveniently used for liquid formulations. If the lymphocytes or compositions are provided as a dry formulation (e.g, freeze dried or a dry powder), a vial with a resilient stopper is normally used, so that the compositions may be easily resuspended by injecting fluid through the resilient stopper. Also contemplated are packages for use in combination with a specific device, such as a syringe or an infusion device such as a minipump, an inhaler, and a nasal administration device (e.g., an atomizer).

The kits may further comprise a suitable set of instructions relating to the use of the lymphocytes and compositions for any of the methods described herein. The instructions generally include information as to dosage, dosing schedule, and route of administration for the intended method of use. Instructions supplied in the kits can be written instructions on a label or package insert (e.g., a paper sheet included in the kit), or machine-readable instructions (e.g., instructions carried on a magnetic or optical storage disk).

Aspects of the Disclosure

Aspect 1. A non-cytotoxic lymphocyte for adoptive cell therapy, wherein the lymphocyte has been engineered to have reduced or silenced perforin expression or activity, and wherein the lymphocyte has been engineered to express at least one therapeutic nucleic acid or polypeptide.

Aspect 2. The recombinant lymphocyte of aspect 1, wherein perforin expression has been silenced with an siRNA, shRNA, gRNA, or antisense oligonucleotide with complementary binding to PRF1 genomic DNA or mRNA.

Aspect 3. The recombinant lymphocyte of aspect 1 or 2, wherein perforin expression has been knocked out by homologous recombination or gene editing of the PRF1 gene.

Aspect 4. The recombinant lymphocyte of aspect 1, wherein perforin activity has been inhibited with a benzenesulphonamide-based perforin inhibitor.

Aspect 5. The recombinant lymphocyte of any one of aspects 1 to 4, wherein the lymphocyte is a T cell, Tumor Infiltrating Lymphocyte (TIL), an Antibody-Coupled T cell Receptor (ACTR), or a natural killer (NK) cell.

Aspect 6. The recombinant lymphocyte of any one of aspects 1 to 5, wherein the lymphocyte is further engineered to express a targeting molecule.

Aspect 7. The recombinant lymphocyte of any one of aspects 1 to 8, wherein the targeting molecule is a ligand, receptor, antibody, or fragment thereof capable of binding a target cell.

Aspect 8. The recombinant lymphocyte of aspect 7, wherein the targeting molecule is a bi-specific antibody.

Aspect 9. The recombinant lymphocyte of aspect 7, wherein the targeting molecule is a chimeric antigen receptor (CAR) or a modified T cell receptor (TCR).

Aspect 10. The recombinant lymphocyte of any one of aspects 1 to 9, wherein the therapeutic polypeptide is an anti-cancer peptide.

Aspect 11. The recombinant lymphocyte of any one of aspects 1 to 9, wherein the therapeutic polypeptide is a heterologous anti-inflammatory cytokine or chemokine.

Aspect 12. The recombinant lymphocyte of aspect 11, wherein the anti-inflammatory cytokine or chemokine is selected from the group consisting of IL2, IL12, IL21, TRAIL, CCL5, GM-CSF, Flt3L, IFNα, and IFNγ.

Aspect 13. The recombinant lymphocyte of any one of aspects 1 to 9, wherein the therapeutic polypeptide is a growth factor, soluble receptor, or enzyme.

Aspect 14. The recombinant lymphocyte of aspect 13, wherein therapeutic polypeptide is selected from the group consisting of an erythropoietin, epidermal growth factor (EGF), alpha-galactosidase A, insulin, fibroblast growth factor 21 (FGF21), αKlotho, and soluble transforming growth factor-β receptor 2 (sTGFβR2).

Aspect 15. The recombinant lymphocyte of any one of aspects 1 to 14, wherein the therapeutic nucleic acid or polypeptide is an antigen or ligand, wherein the non-cytotoxic lymphocyte functions as a cellular vaccine.

Aspect 16. A method for reducing cytotoxicity of a lymphocyte, comprising administering to the lymphocyte an effective amount of a perforin inhibitor.

Aspect 17. The method of aspect 16, wherein the perforin inhibitor comprises an siRNA, shRNA, gRNA, or antisense oligonucleotide with complementary binding to PRF1 genomic DNA or mRNA.

Aspect 18. The method of aspect 16 or 17, wherein the perforin inhibitor comprises a benzenesulphonamide-based perforin inhibitor.

Aspect 19. The method of any one of aspects 16 to 18, wherein the lymphocyte is a T cell, Tumor Infiltrating Lymphocyte (TIL), an Antibody-Coupled T cell Receptor (ACTR), a natural killer (NK) cell, or a T cell with modified T cell receptors (TCRs).

Aspect 20. A method for treating cancer in a subject, comprising administering to the subject an effective amount of the recombinant lymphocyte of any one of aspects 1 to 15.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Transposon Engineering of Antigen-Specific T Cells

Based on a number of inherent properties of antigen specific CD8+ T lymphocytes (T cells), this cell type was selected to serve as a template for engineering a cell based platform that can deliver therapeutic peptide in a user controlled manner. Most importantly T cells can be harvested, expanded in vitro, transposon modified, undergo amplification upon stimulation, and can form stable 'memory' populations in vivo. As a source of antigen specific T cells, the OT1 transgenic T cell receptor (TCR) mouse model was used. OT1 mice exclusively produce T cells which express a transgenic T cell receptor specific for a chicken ovalbumin peptide fragment (termed OVA peptide) presented on H2-Kb. As such, when expose d to H2-Kb presented OVA peptide, these OT1 T cells undergo activation, amplification, and direct cytotoxic effector functions toward the OVA presenting cell. Similar functionality could be elicited in human T cell populations by redirecting the T cells using transgenic TCRs or chimeric antigen receptors responsive to user defined ligands (39).

OT1 T cells were obtained by harvesting spleens from OT1 donor mice and isolating CD8+ cells by magnetic bead sorting. The isolated CD8+ cells can then be expanded in vitro by stimulating with IL2 and anti-CD3e antibodies for 3 days. This yields approximately 70 million CD8+ OT1 cells per donor spleen after expansion. The expanded cells can be efficiently transposon modified leading to stable integration of user defined transgenic constructs. Utilizing the Neon transfection system (ThermoFisher), greater than 35% transfection and efficient transposon integration is routinely obtained as indicated by PCR based detection of post transposition vector product. Thus, piggyBac can be used to efficiently gene-modify mouse T cells.

Example 2

Transposon Modified Antigen-Specific T Cells can be Stably Engrafted

Figure 1B:
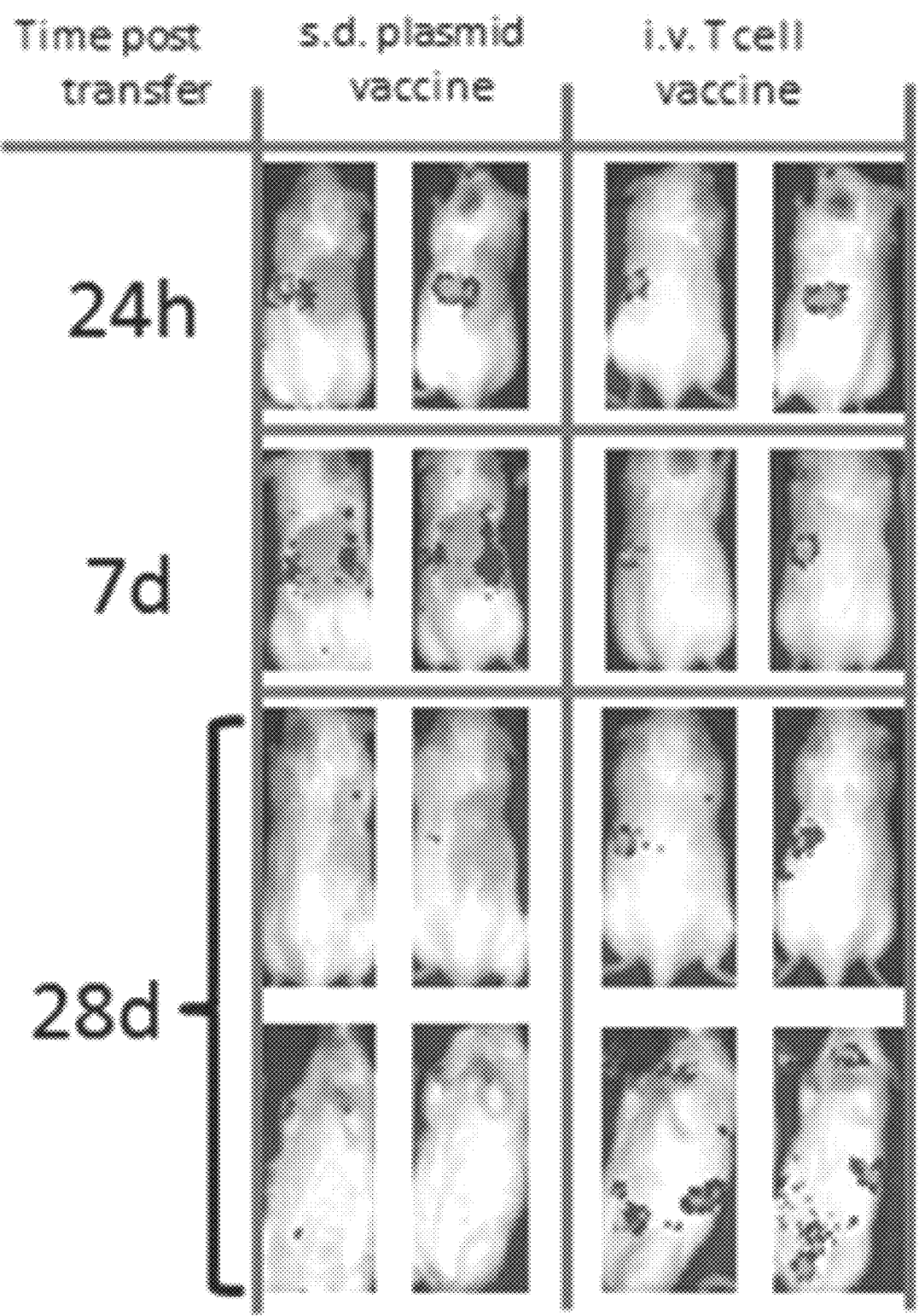
Figure 2A:
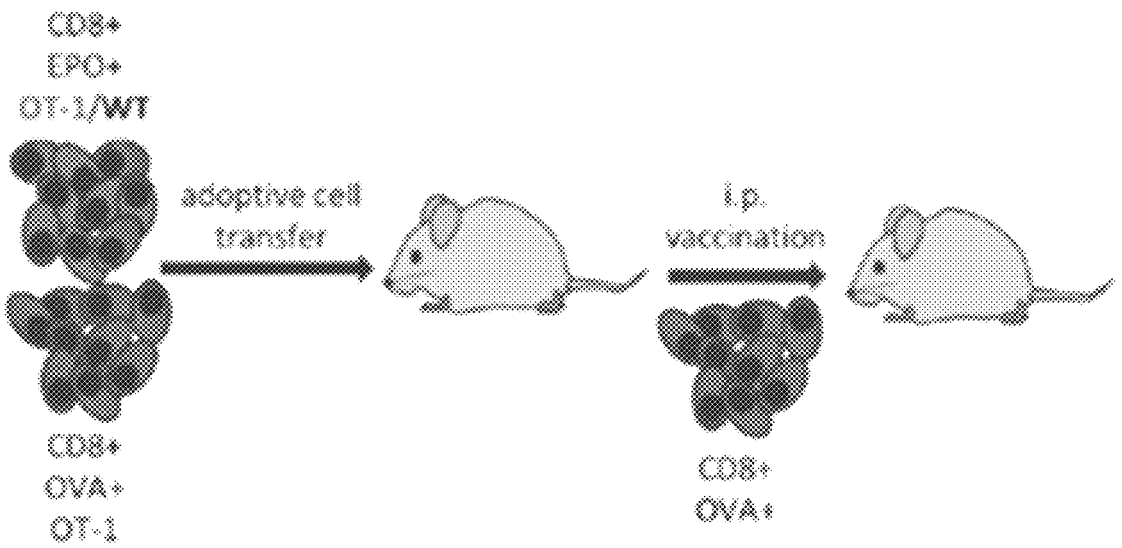
FIGS. 2A to 2C show long term peptide delivery by transposon engineered T cells.
Figure 2B:
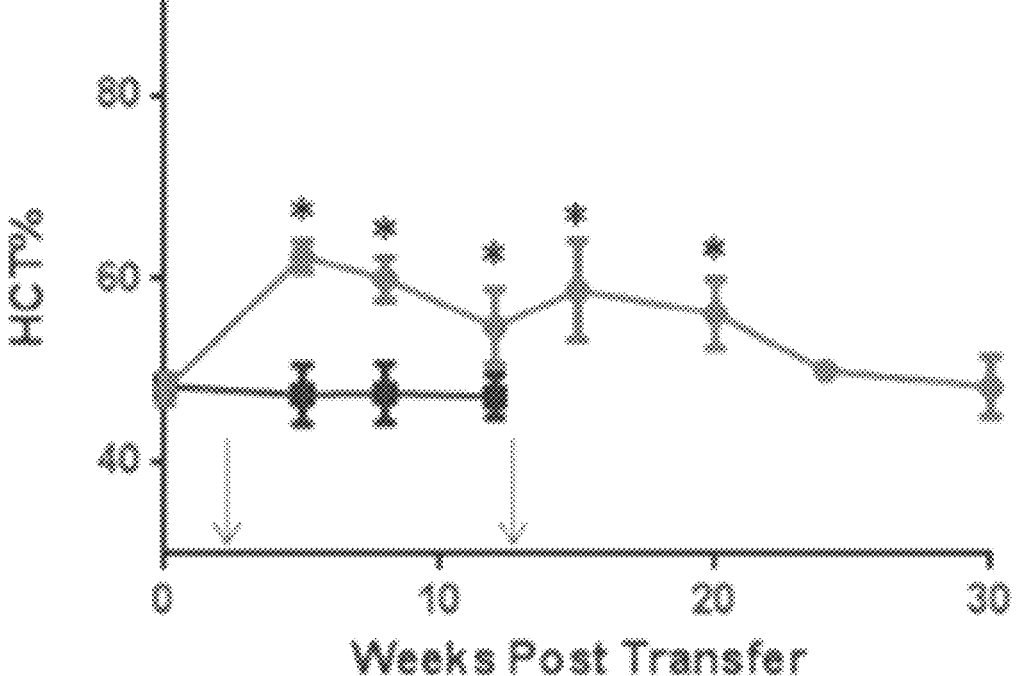
Figure 2C:
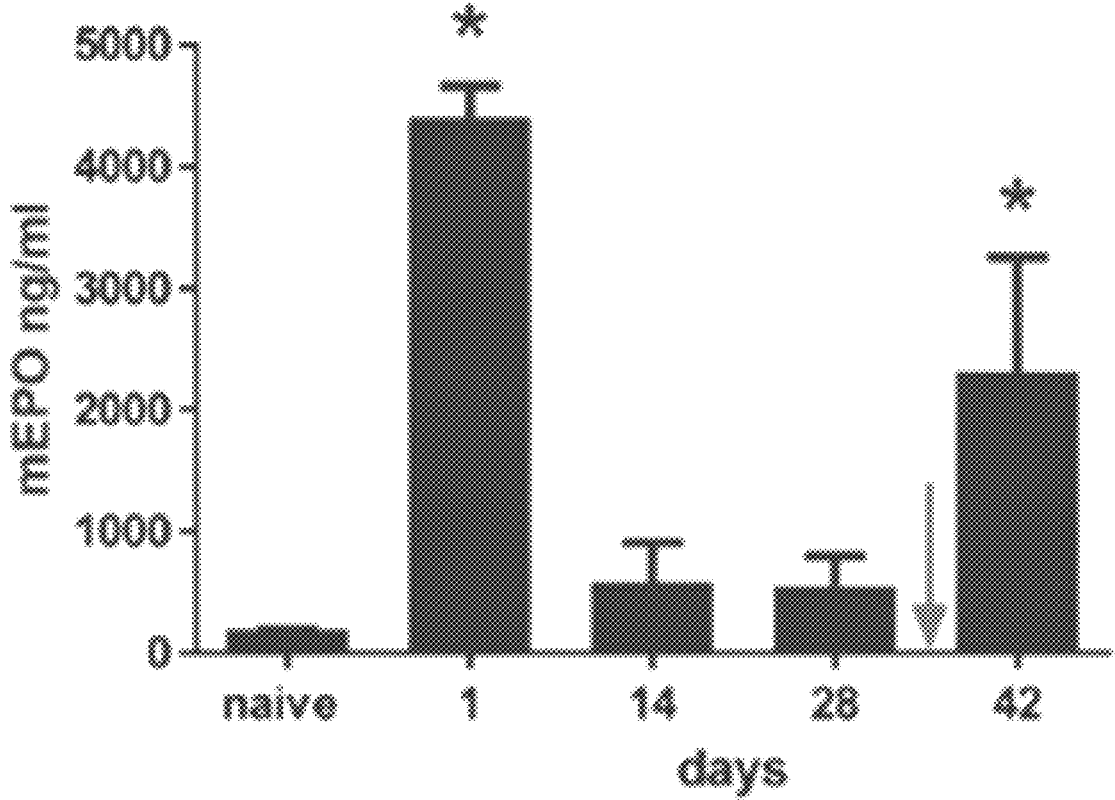

Models utilizing adoptive transfer of OT1 T cells have been used previously to study various aspects of effector T cell function. Transient engraftment of activated OT1 T cells can be achieved in syngeneic host mice by i.v. injection of cells into tail vein. However, the transferred T cells undergo cell death within a few days if not appropriately stimulated. Because OT1 TCRs only respond to OVA peptide presented on H2-Kb, antigenic stimulation must be provided by H2-Kb restricted cells. This can be achieved using an in situ plasmid vaccination administered sub-dermally (s.d.). This leads to recruitment of adoptively transferred OT1 cells to the vaccine site where they destroy antigen presenting cells and undergo amplification as seen on the left (plasmid vaccine) panels of FIG. 1 at the earlier time intervals. This method of vaccination produced insufficient long-term engraftment of transposon modified T cells in part due to the loss of antigen expressing cells as they were destroyed by OT1 effector function. In an attempt to achieve a stable pool of antigen expressing cells, OT1 T cells were transposon modified with an OVA expression construct (pT-CAG-OVA) generating a population of T cells that could present OVA peptide on H2-Kb and respond to this antigen by undergoing amplification. This would theoretically create a population of self-sustaining antigen presenting cells. An added benefit of using OT1 T cells is that these cells would be predicted to display similar tropism and localization to that expected from the population of OT1 T cells being used to deliver therapeutic peptide. Indeed, when OT1-OVA+ cells are co-transferred with OT1-luciferase+ cells the luciferase+ cells undergo much more robust engraftment. Interestingly, these cells seem to localize to the lymphatic structures where they persist in relatively stable numbers for up to 4 weeks as indicated FIG. 1B (cellular vaccine). Cells adoptively transferred using this vaccination method are observed to persist for more than 300 days after adoptive transfer and robustly respond to 'booster' vaccinations nearly a year after adoptive transfer. When these cells are modified to express the peptide hormone EPO, they can effectively stimulate a sustained elevation of hematocrit in mice for up to 14 weeks FIG. 2. These results indicate that stable engraftment of transposon modified T cells can be achieved using this cellular vaccination protocol.

Example 3

LLC Cancer Model

In order to study lung cancer progression a reliable model system is needed where cells can be frequently observed to metastasize from the primary tumor site by in vivo imaging. Several cancer models have been studied in this way including the two syngenic C57/Bl6 lung cancer models utilizing the lewis lung carcinoma (LLC) NSCLC model. In these model systems luciferase expressing cancer cells are implanted into the lung tissue and metastasis can be monitored by imaging luminescent cell localization on an IVIS200 or similar in vivo imaging system. Metastasis to contralateral lung and ipsilateral cervical LN was observed within 14 days of implanting luciferase modified LLC cells into the lung (FIG. 3) of albino C57Bl6 mice. 8 LLC xenograft transfers were performed in a pilot study and treated half of the mice with LZ-TRAIL modified OT1 cell therapy (m7pB+LZ-TRAIL) on the day of xenograft transfer and half with transposase only (m7pB) transfected OT1 cells. Lymphatic metastases were observed by day 18 in three out of 4 mice that received m7pB only OT1 cells indicating that 75% of xenografts resulted in lymphatic metastasis. Contrarily, none of the mice in the group that received TRAIL expressing cells had observable LN metastasis at day 18 after LLC cell transfer. However, some metastasis to contralateral lung and liver was observed in both groups. These results indicate that visualizing metastasis of luciferase modified LLC cells by in vivo imaging can serve as a useful model for studying cancer progression.

Example 4

Prf$^{null}$ OT1 Cells Engineered to Express CCL5 or TRAIL Retain Tumor Homing Capability and Tumor Directed CCL5 Delivery by Engineered Prfnull OT1 Cells Increases Dendritic Cells in OVA+ Tumors The formation and growth of a solid tumor involves complex interactions with surrounding tissue and with the host immune system. The presence of several types of immune cells within tumor tissue is associated with immune mediated tumor rejection. One such cell type is the natural killer (NK) cell which mediates direct tumor cell lysis in addition to production of chemokines and cytokines that modulate the TME promoting a more immunogenic state. The production of the chemokine CCL5 has recently been identified as a driver of tumor infiltration by another important anti-tumor immune cell type known as the conventional type 1 dendritic cell (cDC1). cDC1 cells are adept at taking up tumor associated antigens and efficiently transporting and presenting these antigens to prime CD8+ cytotoxic effector T cells within the lymphatics. As such, the histologic identification of cDC1 cells within tumor biopsies is associated with more favorable prognosis in cancer patients.

Figure 4C:
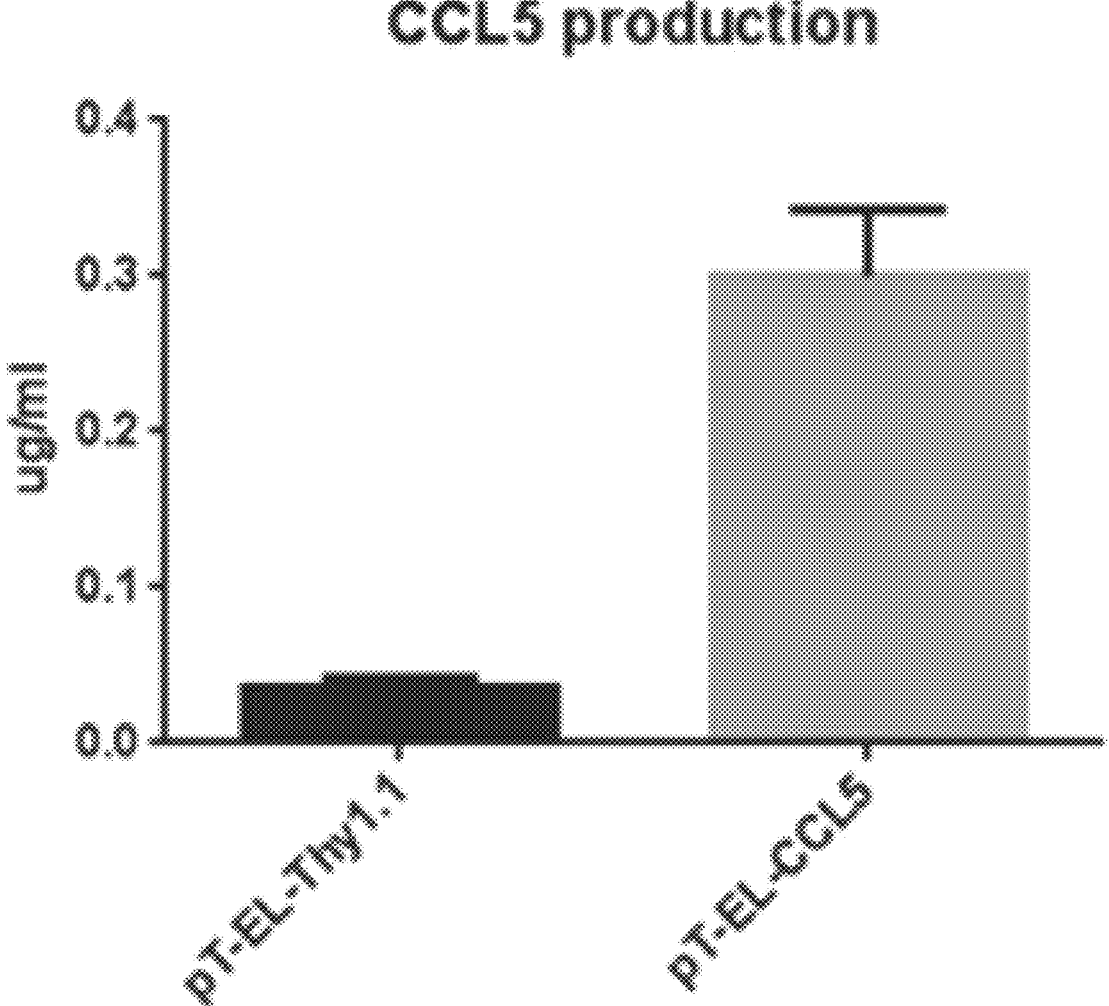

Tumor homing T cells are engineered to express high levels of CCL5 in combination with LZ-TRAIL and evaluate the complimentary effects of an apoptosis inducing and cDC1 recruiting therapy on solid tumor rejection. In an effort to specifically analyze the effects of tumor directed peptide delivery, tumor antigen specific T cells that are not able to lyse tumor cells by conventional means due to loss of the perforin gene (Prf$^{Null}$::OT1+ T cells) are used. Preliminary studies were conducted to confirm that LZ-TRAIL and CCL5 modified Prf$^{Null}$::OT1+ T cells could stably engraft using our adoptive transfer approach and effectively home to tumors expressing cognate OVA antigen (FIG. 4).

Figure 5A:
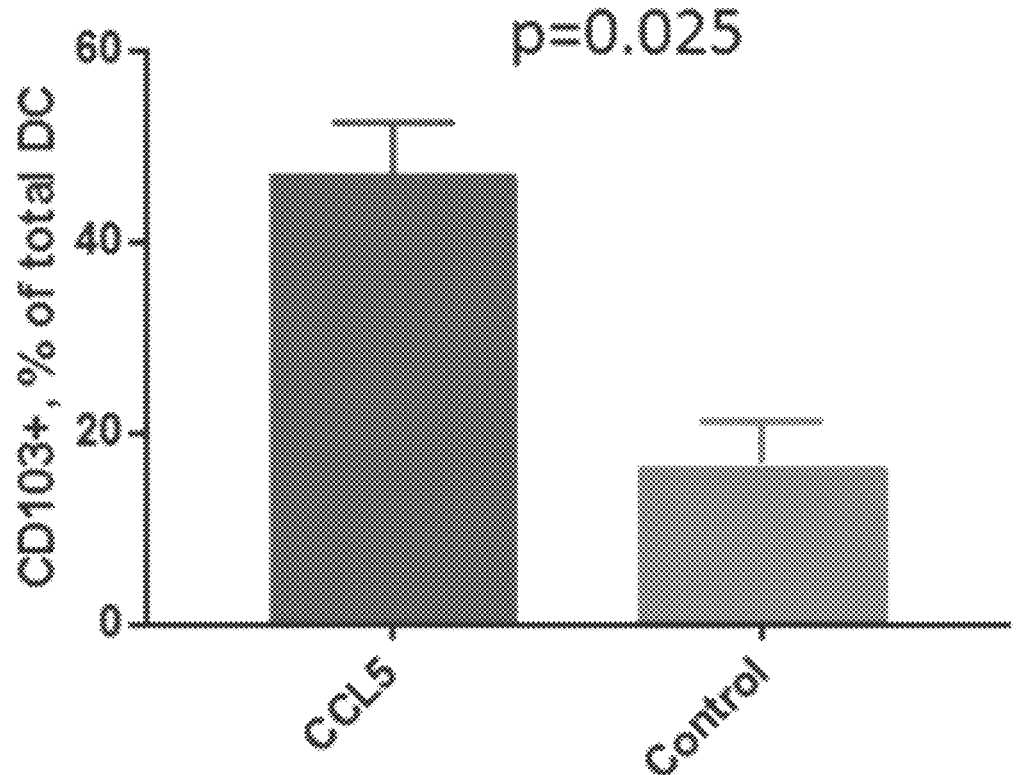
FIGS. 5A and 5B show cytometric analysis of tumors indicates that CCL5 delivery enhances tumoral infiltration of cDC1 cells. Subcutaneous OVA-LLC tumors were implanted and PrfNull OT1 cells engineered to express either pT-ELCCL5 or pT-EL-thy1.1 were adoptively transferred. Tumor tissue was harvested and processed for flow cytometry 48 hours after luminescent signal is observed in the tumor. The results indicated that the percentage of CD103+ dendritic cells in the tumors of mice that received CCL5 engineered cells increased by more than two-fold (FIG. 5A). Representative plots showing gating strategy are shown in FIG. 5B.
Figure 5B:
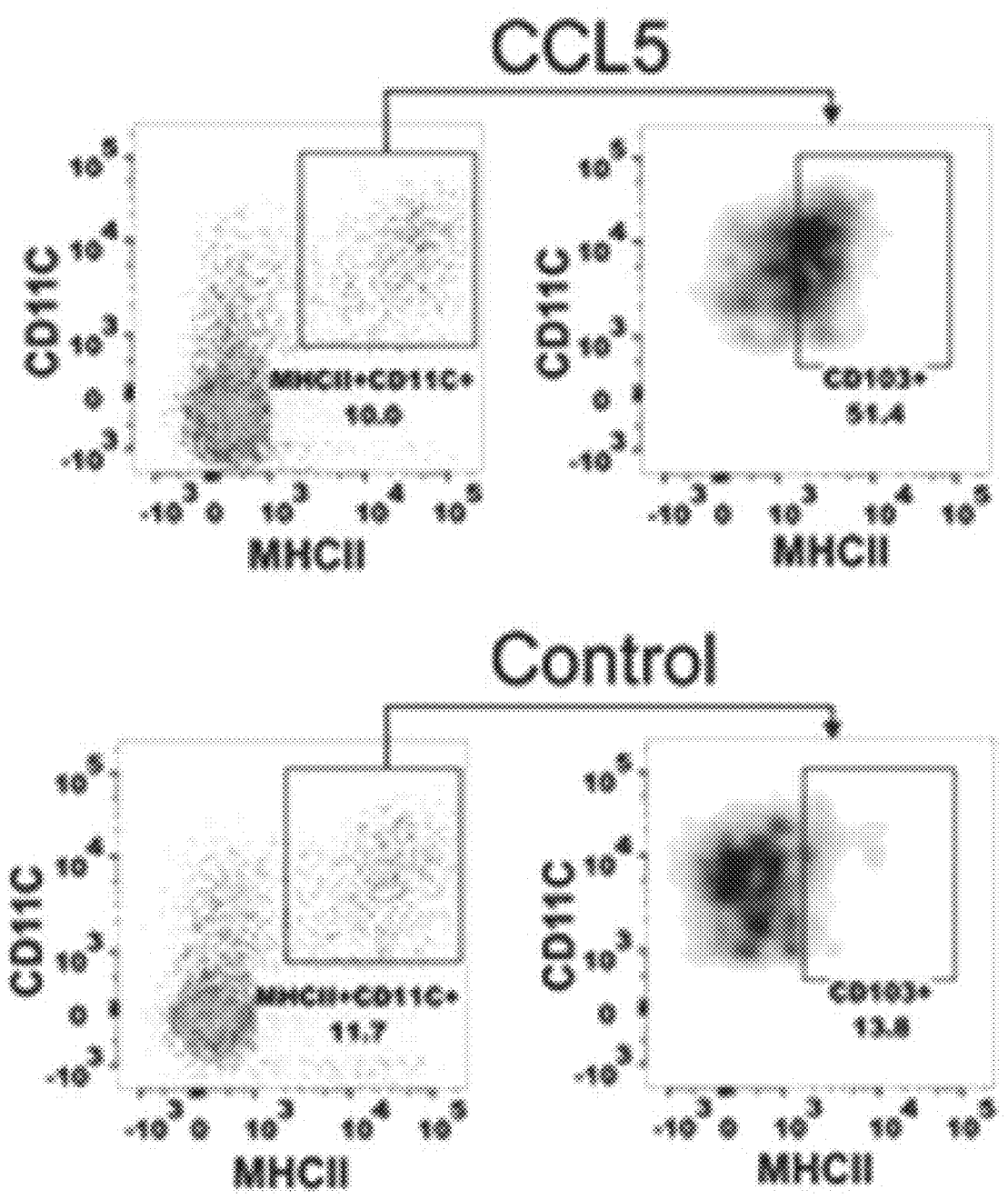

Effective delivery of CCL5 to tumors with engineered tumor homing T cells may promote recruitment of dendritic cells into the tumor. As demonstrated in FIG. 5, there was a more than two-fold increase in dendritic cell recruitment to OVA+LLC tumors when mice were treated with Prf$^{Null}$ OT1 cells engineered to express CCL5. This indicates that the engineered cells are capable of efficiently delivering CCL5 to established tumors and that cDC1 cells efficiently respond to chemokine by infiltrating the TME.

Example 5

Figure 6A:
FIGS. 6A to 6C show transposon modified perforin-KO T cells efficiently home to antigen expressing tumors.
Figure 6B:
Figure 6C:
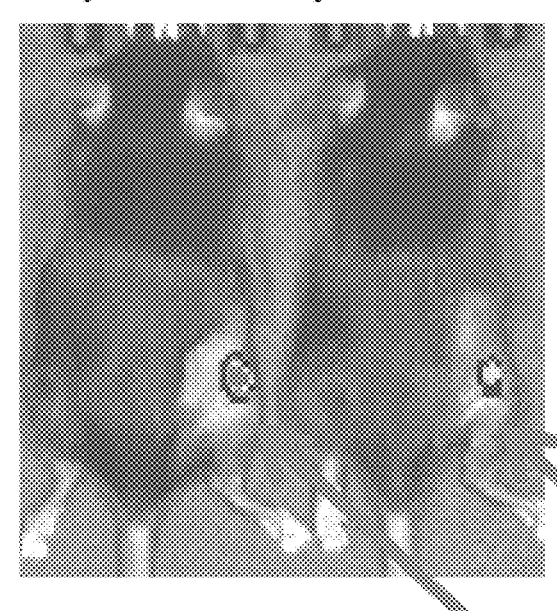

FIGS. 6A to 6C show transposon modified perforin-KO T cells efficiently home to antigen expressing tumors. FIG. 6A shows schematic representation of the transposon used to engineer T cells in this study. (CMV: cytomegalovirus promoter; Luciferase: enhanced firefly luciferase; IRES: internal ribosomal entry site; WPRE: woodchuck poxvirus response element; SV40pA: polyadenylation sequence derived from SV40. FIG. 6B shows luciferase imaging from mice 48 h after adoptive transfer of 5 million luciferase modified OT1 T cells transferred to mice bearing OVA expressing B16 melanoma tumors. FIG. 6C shows luciferase imaging from mice 48 hours after adoptive transfer of 5 million luciferase modified Perforin-KO OT1 T cells.

Figure 7C:
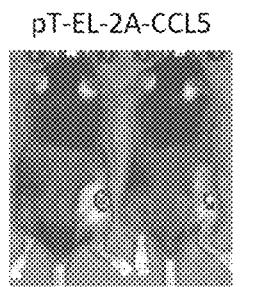
Figure 7C:
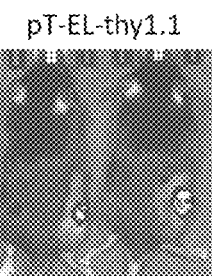
Figure 7C:
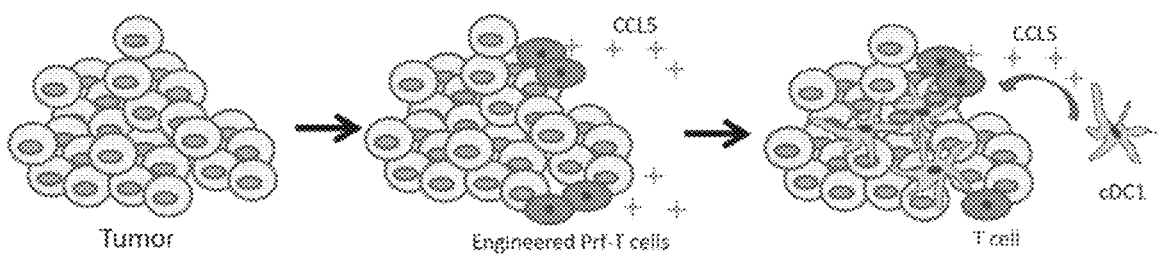

FIGS. 7A to 7C show tumor targeted Prf-T cells engineered to express CCL5 enhance cDC1 infiltration. FIG. 7A shows in vivo imaging demonstrating that Prf-OT1 T cells efficiently home to tumors even when engineered to over express CCL5. FIG. 7B shows flow cytometry was conducted to test the hypothesis that cDC1 dendritic cells are recruited into MC38 tumors and that this is augmented by delivery of CCL5 using Prf-OT1 T cells. FIG. 7C is a schematic of proposed mechanism for facilitating dendritic cell recruitment into solid tumors mediated by Prf-OT1 transposon engineered to express CCL5.

Figure 8A:
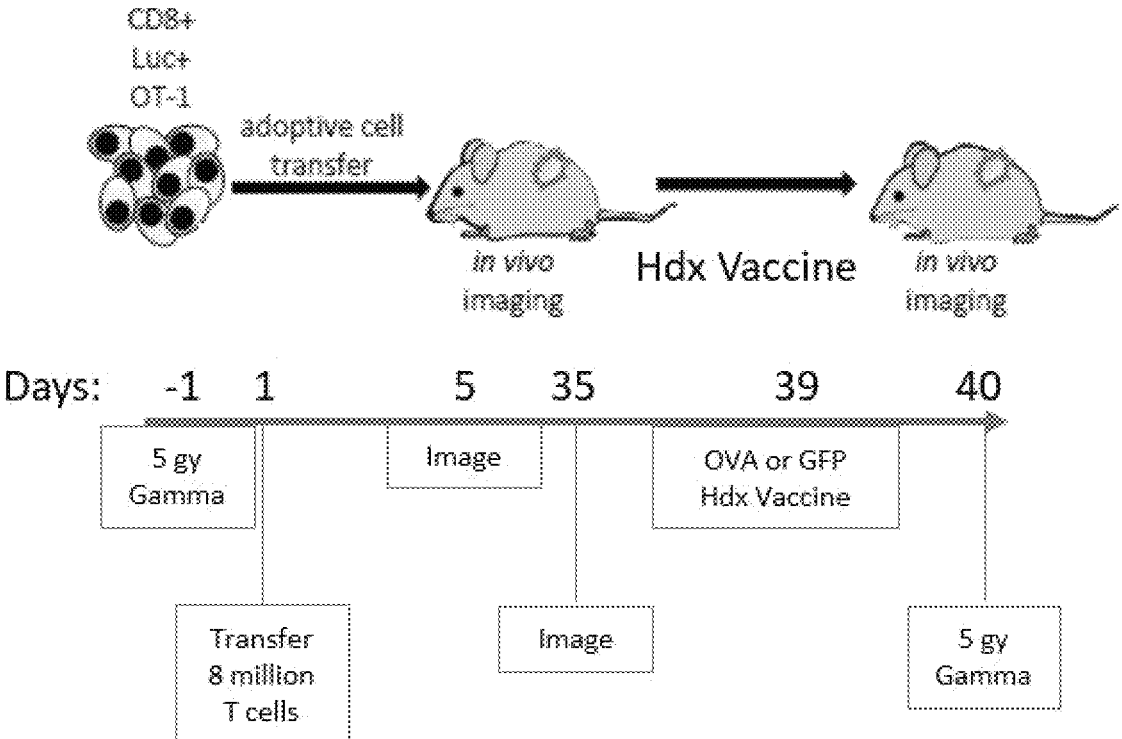
FIGS. 8A to 8C show Prf-T cells retain a memory phenotype upon engraftment.
Figure 8B:
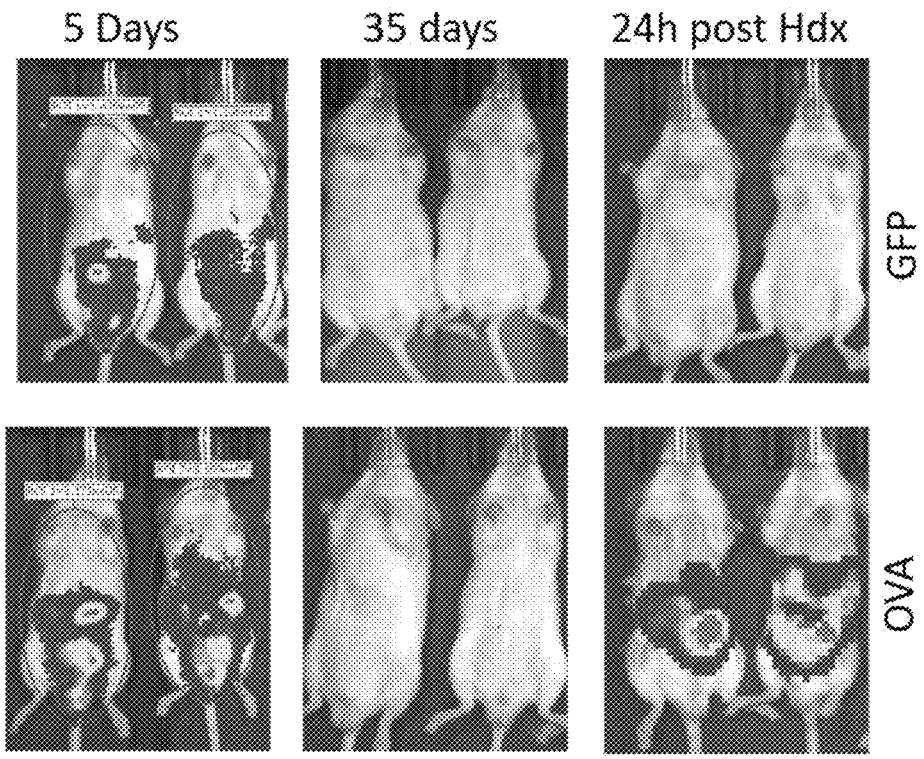
Figure 8C:
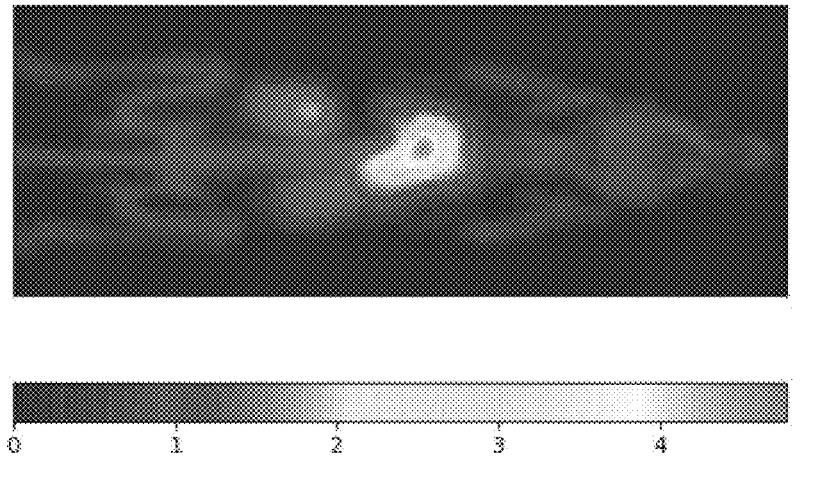

FIGS. 8A to 8C show Prf-T cells retain a memory phenotype upon engraftment. FIG. 8A is a schematic diagram of experimental approach and timeline. Mice were subjected to lymphodepleting irradiation and on the following day they were adoptively transferred with 8 million Prf-OT1 that were transposon engineered to express luciferase. The mice were imaged following adoptive transfer to confirm engraftment. Contraction of T cells was confirmed by imaging at day 35 post adoptive transfer. A hydrodynamic vaccine injection (Hdx) of plasmids driving expression of either GFP (negative control) or chicken ovalbumin peptide which. FIG. 8B, left panels show mice luciferase imaging of mice 5 days after adoptive transfer. FIG. 8B, center panels are images of the same mice on day 35 after transfer. FIG. 8B, left panels are mice imaged 24 hours after adoptive transfer. Note extensive liver infiltration of T cells in OVA group and absence of T cells in GFP group indicating that the response is OVA specific. FIG. 10C shows in vivo plot 3D reconstruction of luciferase signal 5 days after OVA vaccine confirming liver localization of Prf-T cells.

Figure 9A:
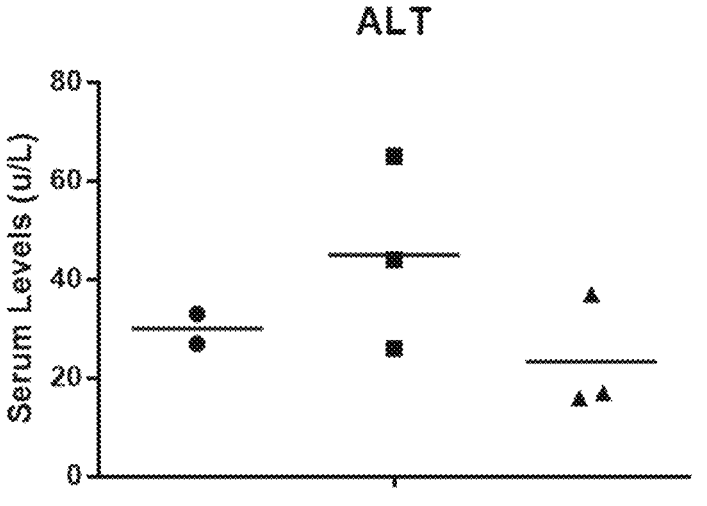
FIGS. 9A and 9B show prolonged infiltration of Perforin Null T cells targeted to the liver by hydrodynamic vaccination does not result in elevated liver enzymes. Blood was harvested 5 days after confirming liver infiltration of T cells by in vivo imaging. ALT (FIG. 9A) and AST (FIG. 9B) levels were not significantly increased in mice that received hydrodynamic OVA vaccine indicating that targeting Prf-OT1 T cells to liver cells does not result in overt damage to the tissue.
Figure 9B:
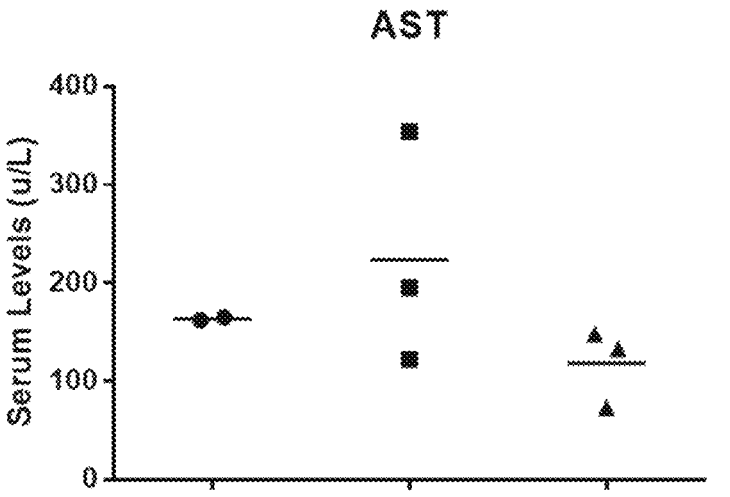

FIGS. 9A and 9B show prolonged infiltration of Perforin Null T cells targeted to the liver by hydrodynamic vaccination does not result in elevated liver enzymes. Blood was harvested 5 days after confirming liver infiltration of T cells by in vivo imaging. ALT (FIG. 9A) and AST (FIG. 9B)

levels were not significantly increased in mice that received hydrodynamic OVA vaccine indicating that targeting Prf-OT1 T cells to liver cells does not result in overt damage to the tissue.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A non-cytotoxic lymphocyte for adoptive cell therapy, wherein the lymphocyte has been engineered to have silenced perforin expression or activity, and wherein the lymphocyte has been engineered to express at least one therapeutic nucleic acid encoding a therapeutic polypeptide or a therapeutic polypeptide, wherein the therapeutic polypeptide is an anti-inflammatory cytokine or chemokine.

2. The recombinant lymphocyte of claim 1, wherein perforin expression has been silenced with an siRNA, shRNA, gRNA, or antisense oligonucleotide with complementary binding to perforin (PRF1) genomic DNA or mRNA.

3. The recombinant lymphocyte of claim 1, wherein perforin expression has been knocked out by homologous recombination or gene editing of the PRF1 gene.

4. The recombinant lymphocyte of claim 1, wherein the lymphocyte is a T cell, Tumor Infiltrating Lymphocyte (TIL), an Antibody-Coupled T cell Receptor (ACTR), or a natural killer (NK) cell.

5. The recombinant lymphocyte of claim 1, wherein the lymphocyte is further engineered to express a targeting molecule.

6. The recombinant lymphocyte of claim 1, wherein the targeting molecule is a ligand, receptor, antibody, or fragment thereof capable of binding a target cell.

7. The recombinant lymphocyte of claim 6, wherein the targeting molecule is a bi-specific antibody.

8. The recombinant lymphocyte of claim 6, wherein the targeting molecule is a chimeric antigen receptor (CAR) or a modified T cell receptor (TCR).

9. The recombinant lymphocyte of claim 1, wherein the anti-inflammatory cytokine or chemokine is selected from the group consisting of IL2, IL12, IL21, TRAIL, CCL5, GM-CSF, Flt3L, IFNα, and IFNγ.

10. The recombinant lymphocyte of claim 1, wherein the therapeutic polypeptide is a growth factor, soluble receptor, or enzyme.

11. The recombinant lymphocyte of claim 10, wherein therapeutic polypeptide is selected from the group consisting of an erythropoietin, epidermal growth factor (EGF), alpha-galactosidase A, insulin, fibroblast growth factor 21 (FGF21), αKlotho, and soluble transforming growth factor-β receptor 2 (sTGFβR2).

12. The recombinant lymphocyte of claim 1, wherein the therapeutic nucleic acid or polypeptide is an antigen or ligand, wherein the non-cytotoxic lymphocyte functions as a cellular vaccine.

13. The recombinant lymphocyte of claim 1, wherein the anti-inflammatory cytokine or chemokine is CCL5.

14. The recombinant lymphocyte of claim 1, wherein the anti-inflammatory cytokine or chemokine is TRAIL.

* * * * *